United States Patent
Wang et al.

(10) Patent No.: US 7,335,889 B2
(45) Date of Patent: Feb. 26, 2008

(54) PMT-BASED PATTERN MATCHING CALIBRATION FOR GAMMA CAMERA USING NON-UNIFORM PINHOLE APERTURE GRID MASK

(75) Inventors: Sharon Xiaorong Wang, Hoffman Estates, IL (US); Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 37 days.

(21) Appl. No.: 11/237,427

(22) Filed: Sep. 28, 2005

(65) Prior Publication Data

US 2006/0065826 A1    Mar. 30, 2006

Related U.S. Application Data

(60) Provisional application No. 60/614,160, filed on Sep. 29, 2004.

(51) Int. Cl.
*G01T 1/00*    (2006.01)

(52) U.S. Cl. ................................. 250/363.09

(58) Field of Classification Search ........... 250/363.07, 250/363.09
See application file for complete search history.

(56) References Cited

U.S. PATENT DOCUMENTS 3,745,345 A * 7/1973 Muehllehner .......... 250/363.01
5,689,116 A * 11/1997 Heukensfeldt Jansen ................... 250/363.09

* cited by examiner

*Primary Examiner*—Constantine Hannaher

(57) ABSTRACT

Point source responses of pinhole apertures in a non-uniform grid mask used to spatially calibrate a gamma camera can be modeled as a two-dimensional Gaussian model function. Pinhole data from each pinhole location are added together to generate a complete Gaussian model of the flood image from the mask. The Gaussian model then is subjected to global and PMT-based pattern matching with an actual input flood image obtained using the mask, to obtain a transformed Gaussian model that is more accurately aligned with actual pinhole locations of the mask. The transformed Gaussian model then can be used in a peak detection process for calibration images, which are used to develop LC coefficients for the camera.

14 Claims, 9 Drawing Sheets

PMT-BASED PATTERN MATCHING CALIBRATION FOR GAMMA CAMERA USING NON-UNIFORM PINHOLE APERTURE GRID MASK

CROSS-REFERENCE TO RELATED APPLICATION AND CLAIM FOR PRIORITY

This application claims priority under 35 U.S.C. § 119(e) from copending Provisional Application Ser. No. 60/614,160 filed Sep. 29, 2004.

BACKGROUND

1. Field of the Invention

The present invention relates generally to nuclear medical imaging devices and more particularly relates to calibration of scintillation cameras to enable correction of acquired image data for unavoidable distortions caused by the inherent physical characteristics of the detector head of the scintillation camera, such as crystal thickness and photomultiplier tube parameters.

2. Introduction

In various environments, such as in medical environments, imaging devices can include detectors that detect electromagnetic radiation emitted from radioactive isotopes or the like within a patient. The detectors typically include a sheet of scintillation crystal material that interacts with gamma rays emitted by the isotope to produce photons in the visible light spectrum known as "events." The scintillation camera includes one or more photodetectors such as an array of photomultiplier tubes, which detect the intensity and location of the events and accumulate this data to acquire clinically significant images that are rendered on a computer display for analysis.

Existing scintillation cameras experience spatial distortion that requires linearity correction (LC). The spatial distortion arises from the fact that the spatial coordinates of light events occurring either at the edges of or between adjacent photomultiplier tubes in a photodetector array will be computed differently than the coordinates of events occurring directly over the center of a photomultiplier tube, due to the physical limitations of the photomultiplier tube. A significant amount of effort has been made to developing correction schemes for spatial or linearity distortion (along with, e.g., the companion energy and flood corrections). Existing LC methods can be generally divided into two categories.

A first category is illustrated in U.S. Pat. No. 3,745,345 (the '345 patent) entitled Radiation Imaging Device, the entire disclosure of which is incorporated herein by reference. Here, a camera head is covered by a lead mask having a uniform grid of pinhole apertures. A sheet source of uniform radiation placed adjacent to the mask causes each aperture to illuminate a scintillation crystal located on the opposite side of the mask. The camera then records the detected location of events in the crystal. There is a difference between the (known) location of the pinholes and the detected location of the events as computed by the camera, which is representative of the degree of spatial distortion at the respective locations on the camera face. Accordingly, a correction factor is computed for each location point so as to move the apparent location of an event as detected to its actual location, as determined by the difference computed in the flood source calibration procedure. The correction factors are then stored in an array for later use during acquisition of clinical images.

A second category is illustrated in U.S. Pat. No. 4,212,061 entitled Radiation Signal Processing and U.S. Pat. No. 4,316,257 entitled Dynamic Modification Of Spatial Distortion Correction Capabilities Of Scintillation Camera, which pertain to spatial correction (both the '061 and '257 patents also are incorporated herein in their entirety by reference). For calibration, a lead mask having elongated slit apertures is used. The camera is exposed to a radiation source, first with the mask oriented in x lines and then with the mask oriented in y lines. For each such exposure orientation, a series of transverse peak measurements at select intervals is developed. An analytical expression is generated to represent event coordinates between calibration intervals. Each orientation exposure, thus, produces one of a pair of calibration coordinates, which in turn permit direct correspondence to associated spatial coordinates. Among other deficiencies in this method, this method can take more than one hour of time by itself. It also requires additional preparation such as 'centering and gain'. Moreover, this method requires use of multiple masks wastes time and money and increases equipment downtime.

Although there has been a significant amount of effort applied in the development of procedures for LC, the lead masks used in the processes have received little attention. The flood masks utilized in prior art devices have involved pinhole apertures arranged in a uniform and rectangular distribution (such as depicted in FIGS. 1 and 2 of the '345 patent). This design has a number of deficiencies, such as: a) generating a relatively low number of data points; and b) being less reliable where spatial distortion is more severe, such as near edges of photomultiplier tubes and/or when thicker scintillation crystals are employed. In addition, existing lead masks do not enhance functionality in the overall calibration process, such as to enable shorter calibration times and/or higher accuracies.

The present inventors have co-developed a new type of flood calibration mask having a much denser population of pinhole apertures in a non-uniform grid pattern, which is used in conjunction with a novel Gaussian fit algorithm to obtain a complete pinhole mask image model for LC coefficient generation. A LC coefficient represents a displacement vector of a point from its detected location in an acquired image to an ideal location.

An important step of the LC coefficient generation process is the accurate determination of spatial coordinates of the pinhole positions in the image. The present inventors have discovered that, while an initial estimation of the pinhole coordinates may be derived in an a priori fashion for a particular type of scintillation crystal and PMT configuration, the use of an a priori model pinhole location algorithm achieves less than optimal accuracy over a large distribution of gamma cameras, because of the large differences in physical parameters from camera to camera.

There thus remains a need for improvements in pinhole position estimation so that the a priori model can be accurately aligned to the acquired image on a camera-by-camera basis over a wide distribution of camera physical parameters.

SUMMARY OF THE INVENTION

The preferred embodiments of the present invention can significantly improve upon existing methods and/or apparatus.

According to one aspect of the invention, a method is provided for spatial calibration of a gamma camera including a scintillation crystal and an array of photodetectors optically coupled to the scintillation crystal, comprising the steps of collecting individual point source response data at each of a plurality of pinhole apertures of a mask, modeling the point source response data as a Gaussian function, dividing the sensing area of the crystal into a plurality of regions, adding together Gaussian function data for each of the regions to obtain a plurality of simulated pinhole mask templates, mounting the mask adjacent to the scintillation crystal, acquiring an actual pinhole mask image, pattern matching the simulated pinhole mask templates with corresponding actual pinhole mask image data to obtain a set of transformation parameters, and transforming the Gaussian model of pinhole locations using the transformation parameters to obtain a transformed Gaussian model of pinhole locations, which are used to obtain a complete LC coefficient model for the correction of spatial distortions.

According to another aspect of the invention, apparatus is provided for executing the above calibration method.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by a way of example and not limitation in the accompanying figures, in which.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Figure 1:
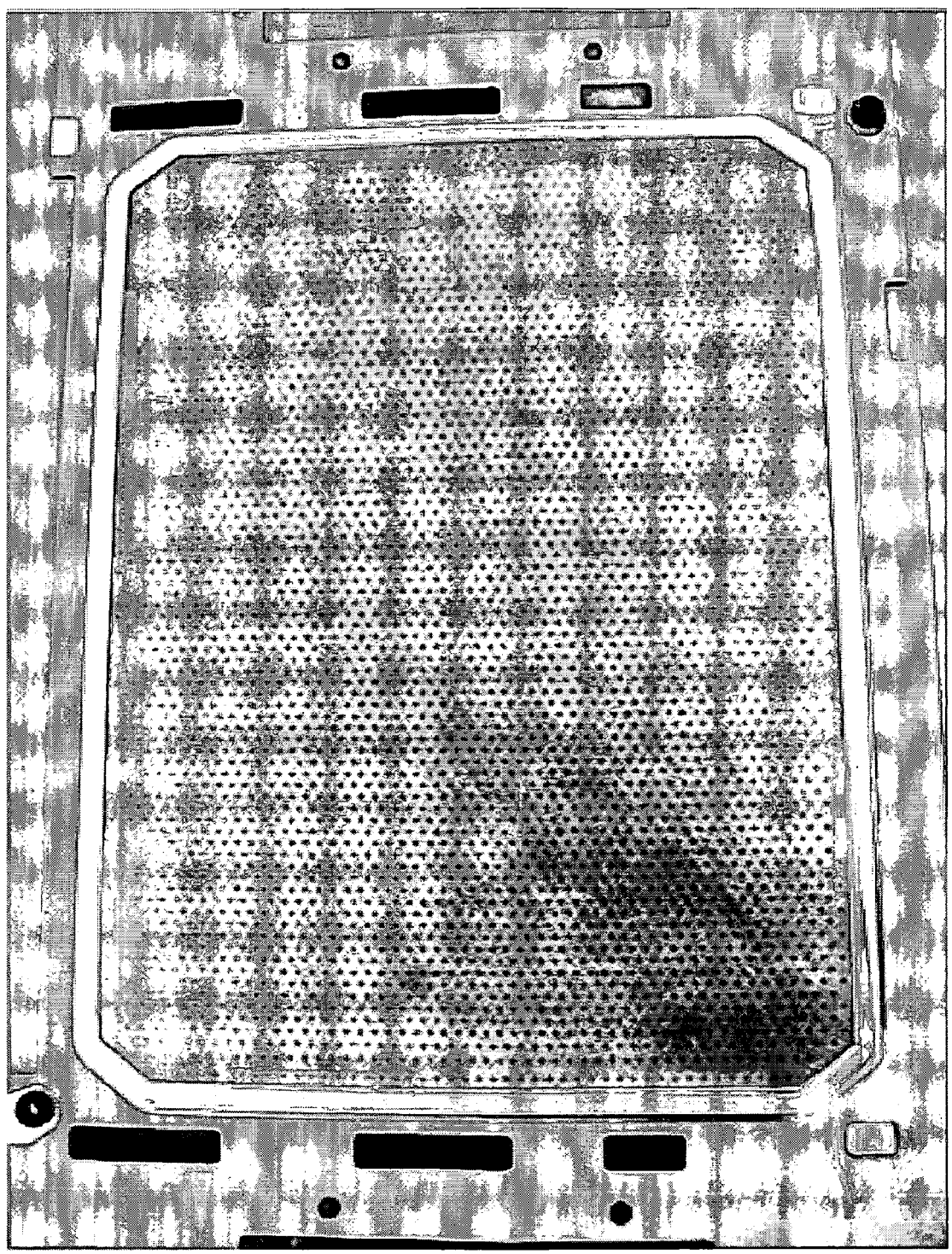
FIG. 1 shows an example of an illustrative embodiment having a lead mask with a non-uniform aperture distribution.
Figure 2:
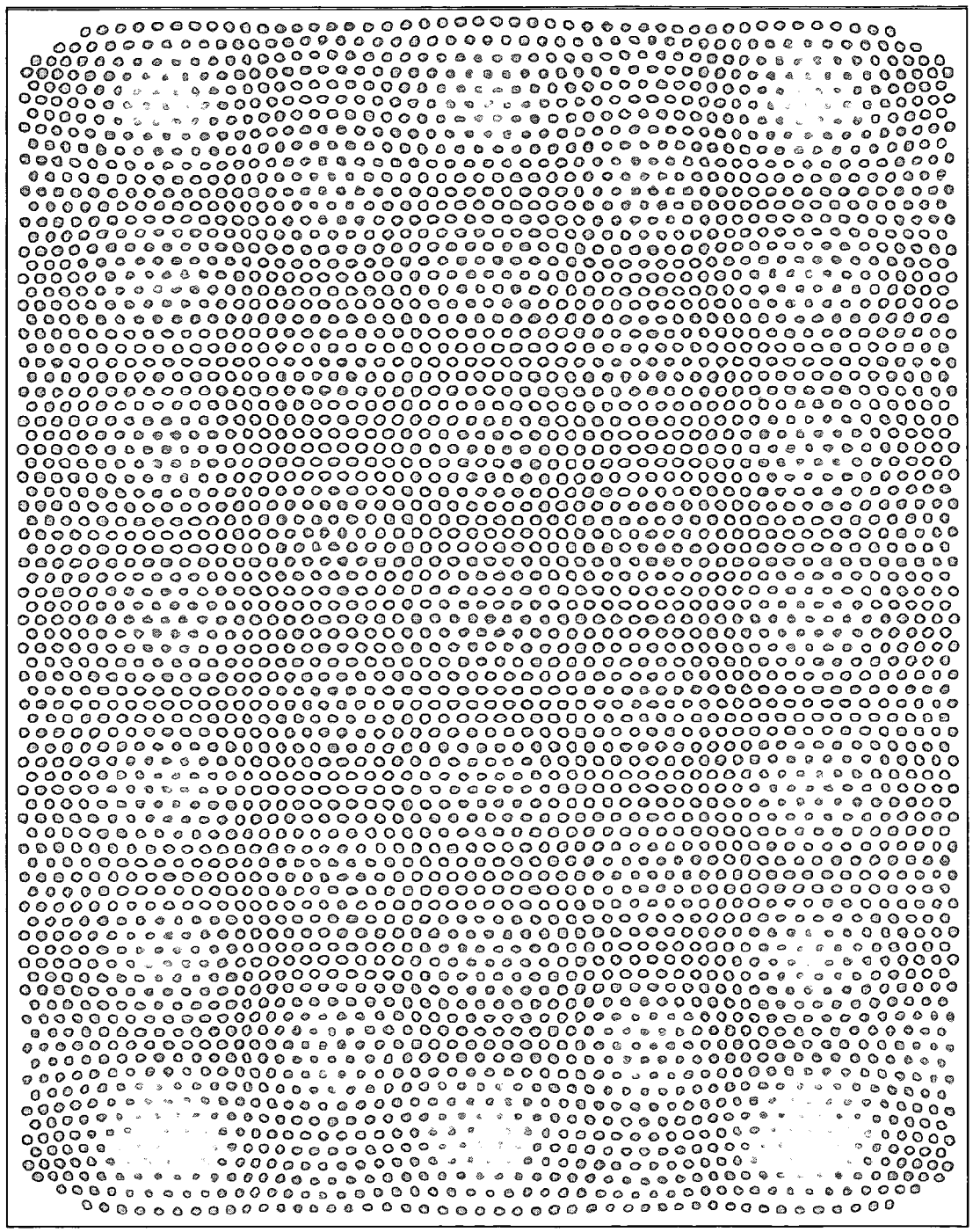
FIG. 2 shows an illustrative image acquired using the mask shown in FIG. 1.

In accordance with the invention, a lead mask is fabricated that can produce pinhole pattern images for obtaining spatial linearity correction coefficients to correct the apparent position of a detected scintillation event to its actual position with high accuracy and reliability. In the preferred embodiments, the mask includes a non-uniform array of pinhole apertures that can achieve this goal, as shown in FIG. 1. An image acquired using the mask of FIG. 1 is shown in FIG. 2. A complete analytical model of the image from the non-uniform grid mask is generated using the individual data set from an X-Y linear scanner with a point source of radiation, which scans the entire mask with the point source of radiation to obtain point source response data at each pinhole aperture, the coordinate location of which is recorded together with the response data. The image model is then divided into a set of templates. The input image and the Gaussian model templates are subjected to a global pattern matching and transformation procedure, and then subjected to a PMT-based pattern matching and transformation procedure, resulting in a better-aligned Gaussian model.

Figure 3:
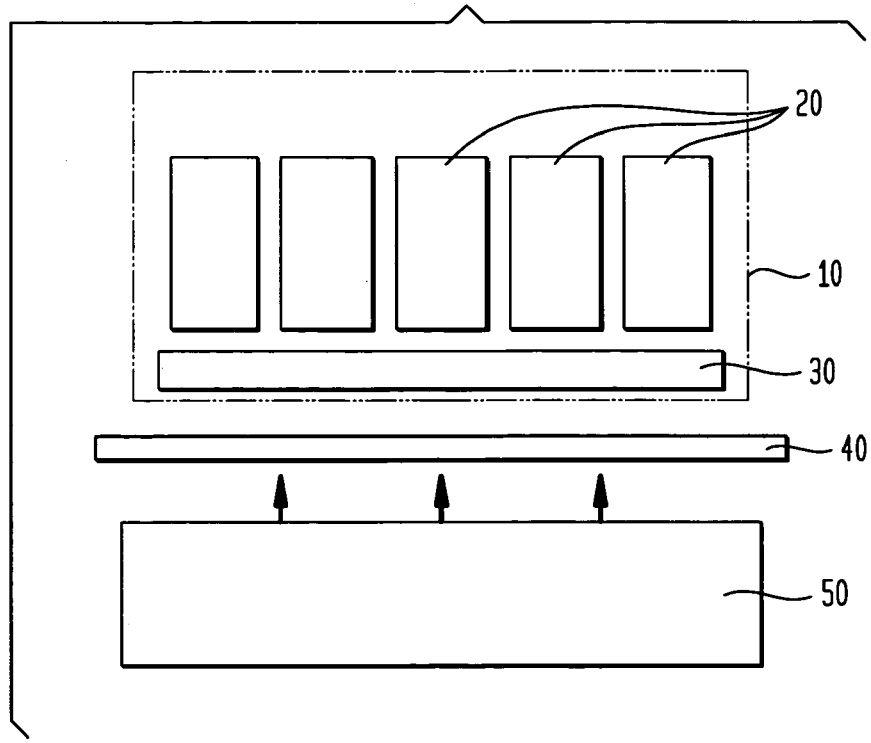
FIG. 3 is a diagram of an illustrative apparatus in which one or more aspects of the present invention may be employed or implemented.
Figure 4A:
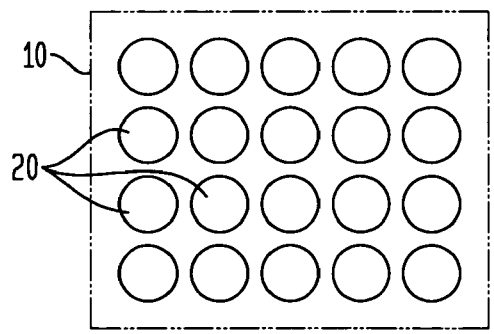
FIGS. 4(A) and 4(B) show illustrative photo-multiplier tube arrangements according to some illustrative and non-limiting embodiments.
Figure 4B:
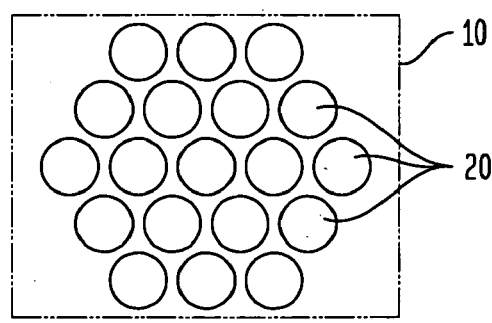

FIG. 3 shows an illustrative implementation including a detector or camera 10, a mask 40, and a radiation source 50. In the illustrated embodiment, a camera 10 includes a scintillation crystal 30 and an array of photo-multiplier tubes 20. FIGS. 4(A) and 4(B) show some illustrative arrangements photo-multiplier tube arrays according to some embodiments shown by way of example only. Other appropriate arrangements could be used based on circumstances.

In use, a uniform sheet source or point source of radiation causes each pinhole aperture of the mask to illuminate a scintillation crystal with gamma photons. The camera then records the apparent location of the resulting light events in the crystal. The non-uniform grid of pinholes is designed so that the image produced can facilitate highly accurate points for location detection. Costs related to camera calibration can be substantially reduced and/or NEMA (National Electrical Manufacturers Association) gamma camera linearity specifications can be substantially improved upon. Various embodiments can be used in various nuclear medicine cameras. Various embodiments may also be used in a variety of radiation and/or other applications where a calibration process is used. In some embodiments, new LC procedures can provide significant time and/or material savings while preserving and/or even improving the detector's performance, exceeding the NEMA requirements.

Model Generation

Model generation involves two components: 1) a set of model patches obtained from the a priori knowledge, which can be stored in a database; and 2) a set of templates that contains the sizes, shapes, and locations of image patches and can be used to circumscribe the input image patches during on-line spatial location computation.

Model generation for a global image match is straightforward, since the data area of the whole image can be used as the model and as the template. Model patch generation for PMT-based patch generation, however, is much more complicated as illustrated in FIG. 9(a)-(e). Because the distortion under each PMT is different, the boundaries between PMT patches are not straight lines but higher ordered curves. In addition, the shape and size of a PMT model patch differs according to the location of the PMT tube, where at the center portion of the field of view (FOV) the patches resemble hexagons but at edges are more like a half or quarter of a hexagon. Furthermore, neighboring PMT patches are interleaved, due to the non-uniform, high-density pinhole aperture grid mask.

To assist in model patch generation, the image model from the non-uniform grid mask must contain signal information from all pinholes in the mask. Because the image model acquired using the mask is a summation of point responses from each pinhole, it is necessary to first obtain a non-overlapped point response for each pinhole, which then serves as the basis for signal decomposition to separate out each individual PMT model patch. For this purpose, a programmable X-Y scanner can be used. The scanner is installed on top of the detector, and can access any point within the Useful Field Of View (UFOV) of the detector. A Cobalt 57 radiation source is mounted on a pinhole collimator containing apertures that are the same as the apertures on the lead mask. The X-Y scanner carries the Co-57 source to each pinhole aperture location on the lead mask, where appropriate counts are collected by the detector in order to model the point source response of each pinhole aperture. The number of counts can be determined by the following formula:

$$n_c = \frac{C}{n} \quad (0)$$

where C is total number of counts desired and n is number of pinholes. The data so acquired from all of the pinhole locations on the mask collectively forms a simulation of a flood image of the mask, while single point source response information is obtained for each individual pinhole aperture location on the mask.

At any location on the mask, the point response data of a pinhole aperture may be modeled as a two-dimensional (2D) Gaussian surface, which can be written as:

$$G(x,y) = c_0 + \lambda e^{-1/2U} \quad (1)$$

where the elliptical function is:

$$U = \left(\frac{x}{\sigma_x}\right)^2 + \left(\frac{y}{\sigma_y}\right)^2 \quad (2)$$

The lengths of the axes of the ellipse U are $2\sigma_x$ and $2\sigma_y$ in the unrotated X and Y axes, respectively. The center of the ellipse U is located at $(x_0, y_0)$. Finally, U is rotated $\tau$ in the clockwise direction from the X axis.

The rotated coordinate system is defined as:

$$\begin{bmatrix} x \\ y \end{bmatrix} = \begin{bmatrix} \cos\tau & -\sin\tau \\ \sin\tau & \cos\tau \end{bmatrix} \begin{bmatrix} x' - x_0 \\ y' - y_0 \end{bmatrix} \quad (3)$$

Figure 5:
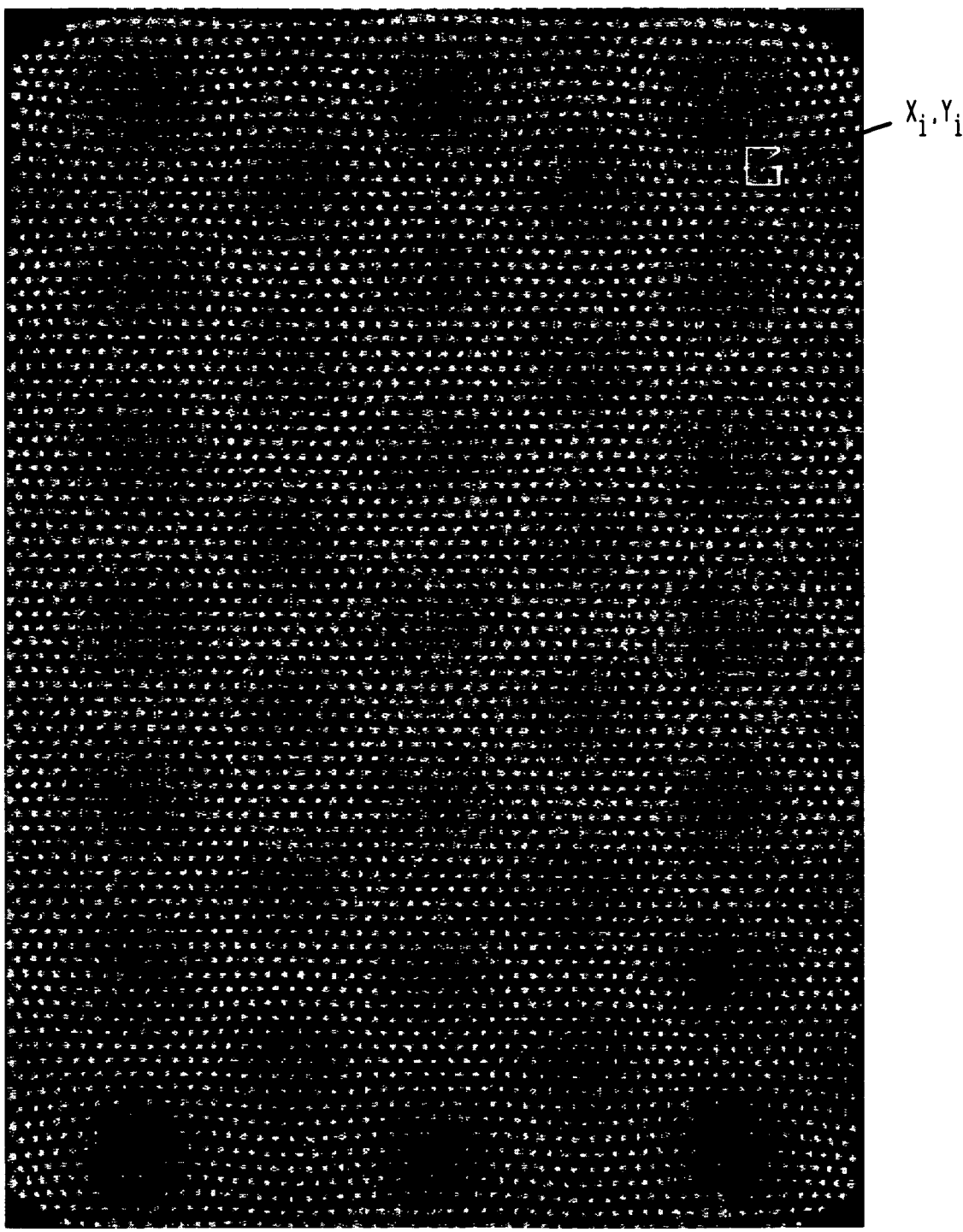
FIG. 5 is an illustrative example of a simulated flood image of the non-uniform pinhole mask obtained by Gaussian modeling.

A point response image is acquired at each pinhole location of the mask by collecting a sufficient number of counts or events and fitting the data with 2D Gaussian function according to Equations (1)-(3) above. The fitted data provides a complete model of the mask calibration image. Adding the individual point response Gaussian functions together produces a simulation flood image of the mask, as shown in FIG. 5.

Once the complete model is obtained, a PMT-based model patch can be determined for each PMT location by the collection of pinhole responses under the PMT, and the application of image processing techniques such as thresholding generates a template that can be used to cut out an image patch from the input image that corresponds to a PMT location of a corresponding PMT model patch.

Pattern Matching Processes

Figure 6:
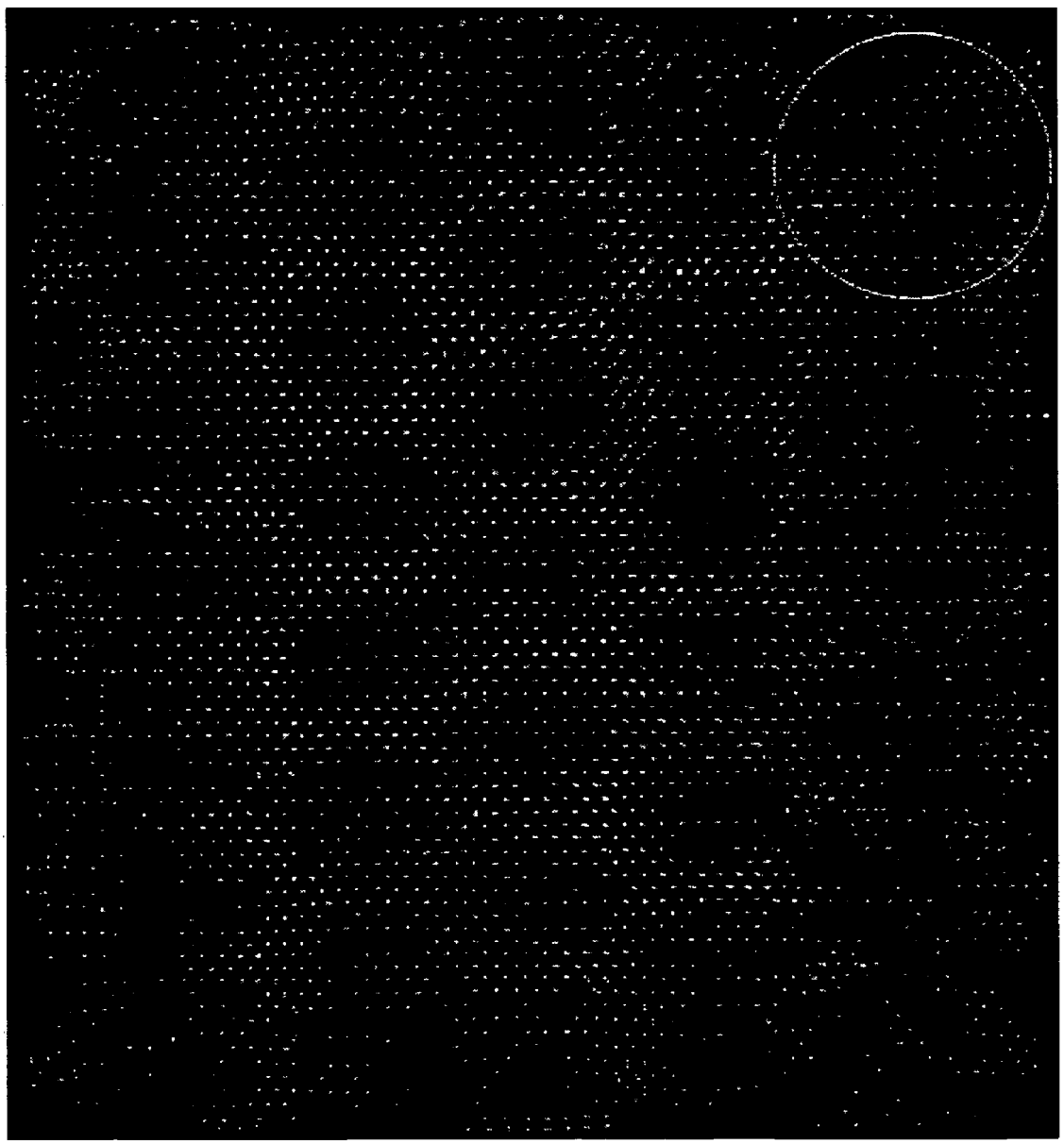
FIG. 6 is an illustrative example of alignment discrepancy between an initial estimation of pinhole aperture positions generated by a Gaussian model and an input image obtained using a pinhole aperture lead mask.

FIG. 6 is a composite of an actual input image obtained from the pinhole mask (example shown in FIG. 2) superposed with the initial estimation of pinhole location obtained from the individual scanned Gaussian model as explained above. FIG. 6 illustrates the discrepancy between actual imaged pinholes and the initial estimation of pinhole locations using the Gaussian model (shown as white dots). It can be seen that the initial Gaussian model contains misalignments with the input image, as many white dots fall between lines of actual imaged pinholes. At the left and right hand side edges, the white dots are misaligned by as much as two rows, which is equivalent to over ten pixels. The area in FIG. 6 marked by a circle illustrates another significantly misaligned portion of the Gaussian model.

Figure 7:
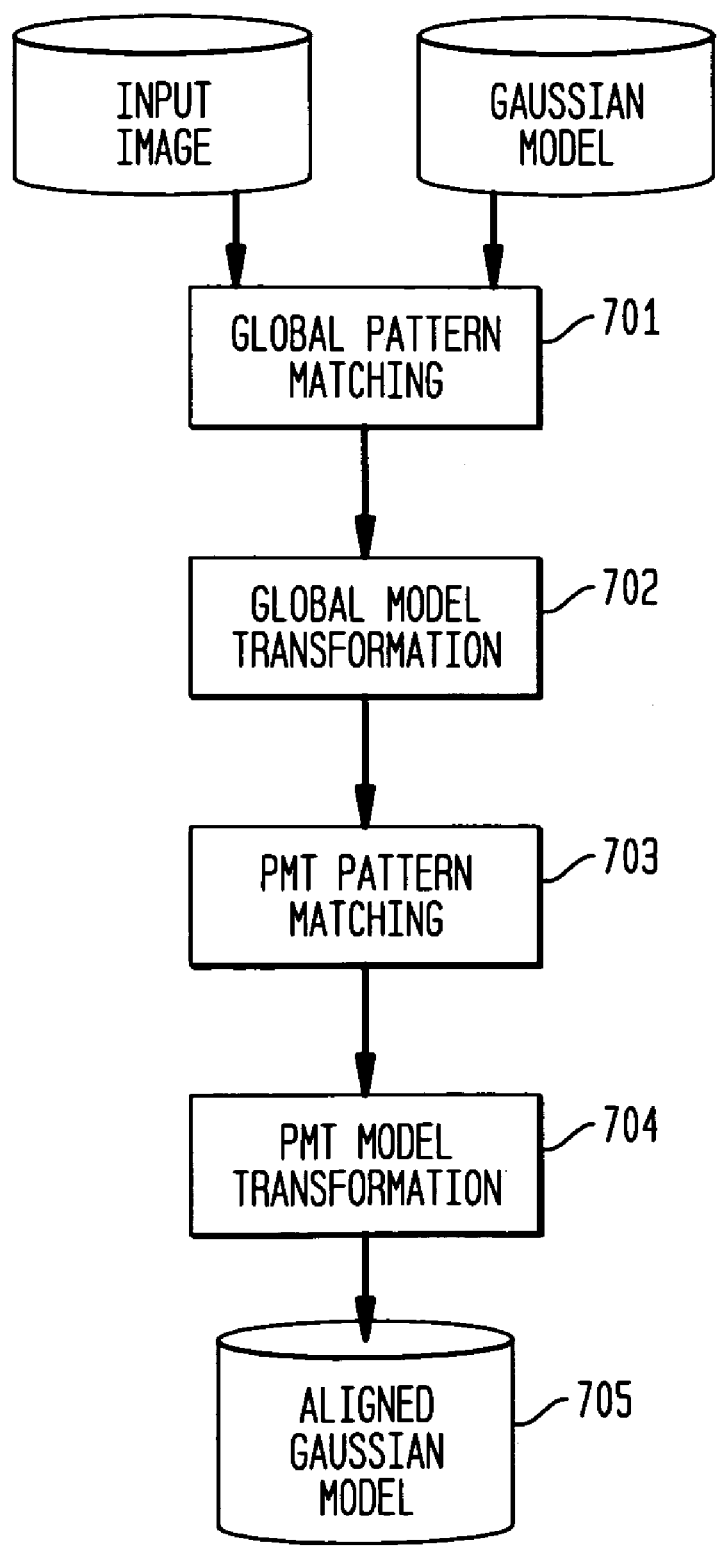
FIG. 7 is a flow diagram of a pattern matching procedure according to a preferred embodiment of the present invention.

According to one preferred embodiment of the present invention, as shown in FIG. 7, the input image and the Gaussian model are first subjected to a global pattern matching algorithm (step 701); the Gaussian model is then modified (transformed) according to the result of the global matching algorithm (step 702); then, the Gaussian model is further refined at the PMT level by pattern matching between input image and Gaussian model by using PMT-unit image patches (step 703); following this step, the Gaussian model is further transformed in accordance with the results of the PMT-based pattern matching (step 704), so as to obtain an improved aligned Gaussian model (step 705).

According to one preferred embodiment, the transformations are derived using a pattern matching algorithm that optimizes two displacement and two magnification parameters to minimize the difference between the Gaussian model and the input image in the least squares sense. In the global matching step, the entire Gaussian model image is transformed using the four parameters; in the PMT-based matching step, small image patches under each PMT are "cut" or extracted from the input image according to the size, location, and shape of the corresponding PMT Gaussian model patch. For each patch pair, the four parameters are calculated and applied. Thus, for a detector having M PMTs (where M is an integer), the combination of all transformations results in a Gaussian model transformed in 4(1+M) degrees of freedom, which is sufficient for the degree of alignment desired.

The global pattern matching and PMT-based pattern matching both can share the same algorithm because both inputs are in the form of image data. The goal of the pattern-matching procedure is to align the Gaussian model with the acquired input image using the pinhole aperture mask, to obtain a set of more accurate estimations of pinhole positions for peak detection algorithms in order to attain a spatially calibrated detector.

We have determined through experimentation that a four parameter (i.e., two displacement factors and two magnification factors) transformation represents an optimized tradeoff between the degree of accuracy of the registration of the Gaussian model to the pinhole aperture mask and the required computational resources (time and cost) to accomplish the desired results. However, it will be apparent to those skilled in the art that more or less than four transformation parameters also could be used where the equilibrium point of the tradeoff considerations is moved.

Pattern Matching Algorithm

We denote the acquired pinhole pattern image as f(x,y) ($-N/2 \leq x$, $y \leq N/2$), where N is the size of the image in pixels, and the ideal Gaussian model as g(x,y) ($-N/2 \leq x$, $y \leq N/2$). If the parameters for the transformation include the displacement of g(x,y) with respect to f(x,y) (denoted as $x_0$ and $y_0$), and scaling or magnification factors along the x and y axes (denoted as $l_x$ and $l_y$), then the transformation can be expressed as $$\mathcal{T}_X\{g(x, y)\} = g\left(\frac{(x-x_0)}{l_x}, \frac{(y-y_0)}{l_y}\right) \quad (4)$$

where $$X = \{x_0, y_0, l_x, l_y\} \quad (5)$$

Then, the objective function for optimization can be written as $$\Psi(X) = \iint [f(x,y) - \mathcal{T}_X\{g(x, y)\}]^2 dx dy \quad (6)$$

In principle, any multidimensional minimization technique can be used to resolve the transformation parameters X. Experimental tests have shown that a simple downhill simplex method works well. The downhill simplex method is not as efficient as Powell's method and usually requires more function evaluations; however, the simplex method requires only function evaluations and not derivatives, and may be less likely to fall into local minima due to the repetitive nature of the pinhole mask, and is therefore more reliable than Powell's method.

Figure 8:
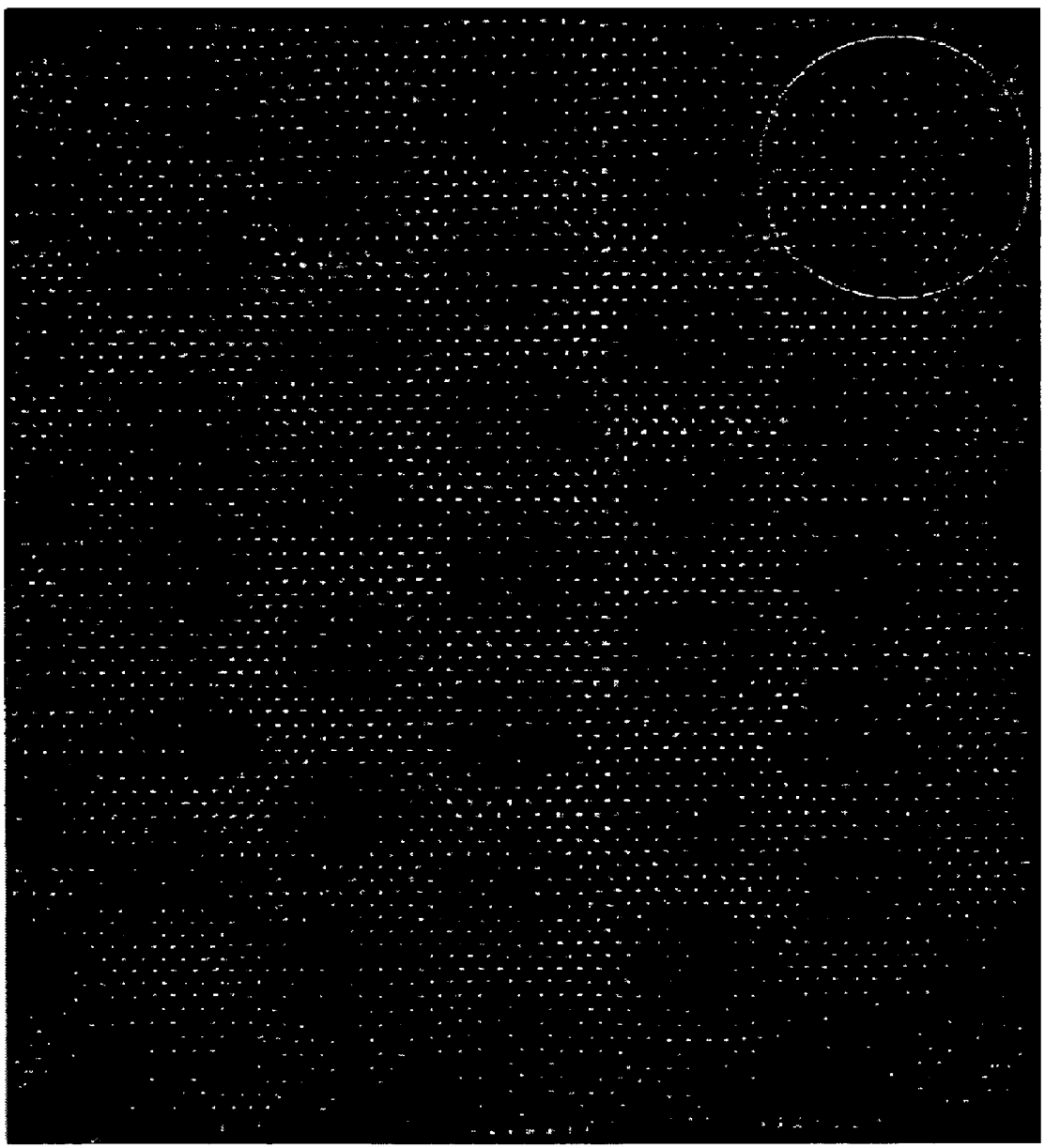
FIG. 8 is an illustrative example showing modified Gaussian modeled pinhole locations as a result of global pattern matching according to the present invention.

Referring again to FIG. 7, at step 701 the input image and the Gaussian model are used to determine a global transformation X, using the objective function defined by Equation (6). The global transformation applies a rigid body displacement and magnification (scaling) along the x and y axes. FIG. 8 shows the result of the global transformation (step 702 of FIG. 7), using the transformation factors obtained by the global pattern matching. As can be seen, the majority of white dots displaced from actual imaged pinholes are corrected. Left and right hand side edge dot misalignments are reduced to three or fewer pixels, and most white dots in the encircled area have been aligned correctly, although there remain a number of dots that do not lie correctly at the center.

Figure 9A:
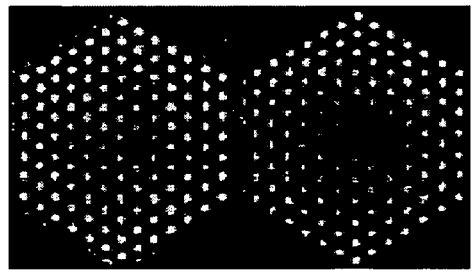
FIGS. 9(A)-9(E) show examples of PMT-based pattern matching according to the present invention.
Figure 9B:
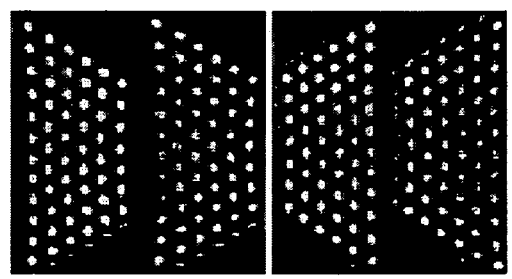
Figure 9C:
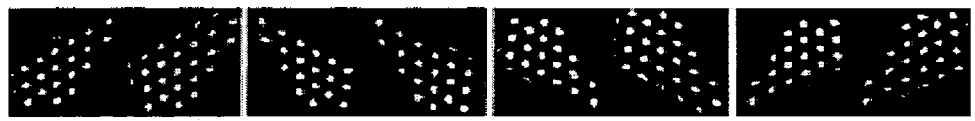
Figure 9D:
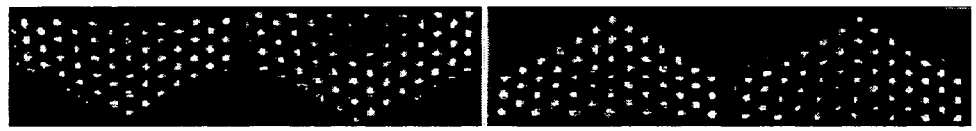
Figure 9E:
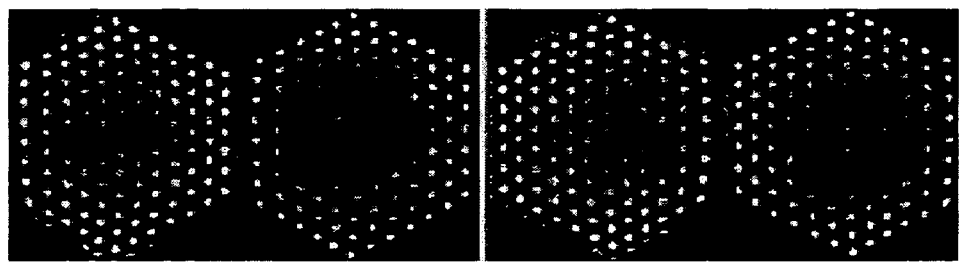

At the next step 703, the Gaussian model is subjected to further refinement at the PMT level. Because location computation using Anger logic is largely PMT dependent, the group of dots under a single PMT tend to have a similar magnification and displacement. For each PMT, then, an image "patch" is selected or "cut" for both the input image and the Gaussian model, to thereby obtain a patch pair. Equation (6) is then used to match the patch pair, obtaining transformation factors for each patch pair, with overlapped points being averaged. FIGS. 9(A)-9(E) show respective image patch pair examples cut from different PMT units. For each PMT unit, there is a specific patch defined to achieve the best match. FIG. 9(A) shows a patch located at the center portion of the PMT; FIG. 9(B) shows patches at right and left hand sides of PMTs; FIG. 9(C) shows PMT corner patches; FIG. 9(D) shows PMT bottom and top patches; and FIG. 9(E) shows PMT patches at left and right hand side edges of the detector, next to 2 inch tubes. Upon completion of PMT patch pair minimization calculation using Equation (6), the globally transformed Gaussian model is subjected to PMT-based model transformation at step 704.

Figure 10:
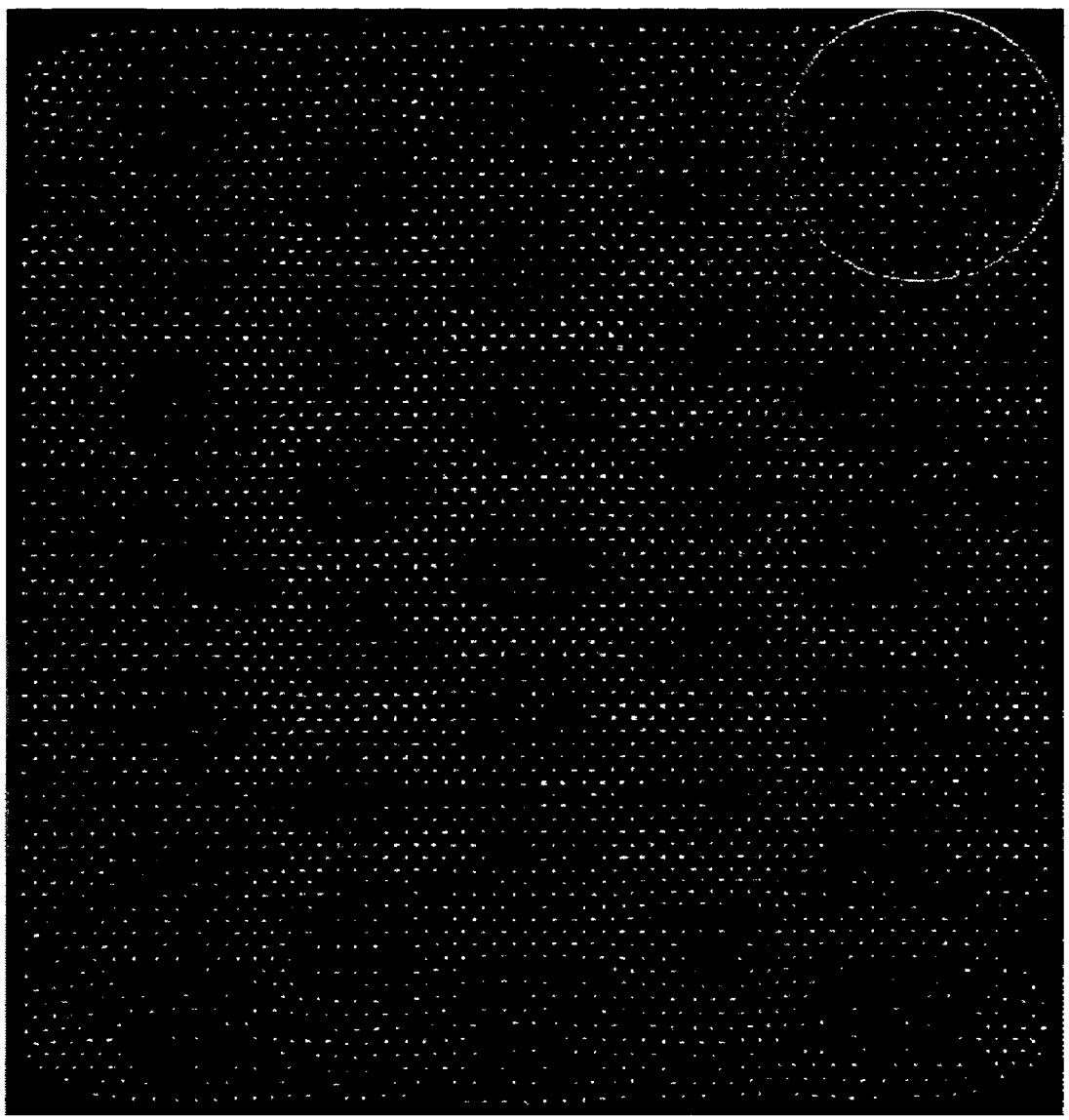
FIG. 10 is an illustrative example showing modified Gaussian modeled pinhole locations as a result of PMT-based pattern matching according to the present invention.

FIG. 10 shows an example of the aligned Gaussian model obtained at step 705, after global and PMT-based pattern match transformation. As can be seen, after the PMT-based pattern matching, the Gaussian modeled pinhole locations as represented by the white dots are transformed by displacement and magnification factors obtained for each PMT unit, resulting in a much more accurate alignment of the Gaussian model with the actual input image.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. Apparatus for spatial calibration of a gamma camera including a scintillation crystal and an array of photodetectors optically coupled to the scintillation crystal, comprising:
   a) a mask having a plurality of pinhole apertures arrayed in a non-rectangular distribution;
   b) a point source of radiation capable of being scanned over the entirety of said plurality of pinhole apertures; and
   c) a processor for collecting individual point source response data from each of said plurality of pinhole apertures, modeling said point source response data as a Gaussian function, generating at least one Gaussian model patch for the entirety of said mask, transforming said Gaussian model patch using a set of alignment transformation parameters, and using said transformed Gaussian model patch to correct input image data for spatial distortions.

2. The apparatus of claim 1, wherein said array of photodetectors comprises an array of photomultiplier tubes.

3. The apparatus of claim 1, wherein said set of alignment transformation parameters are obtained from pattern matching said Gaussian model patch with an actual input image obtained using said mask.

4. The apparatus of claim 3, wherein said pattern matching is performed on a global basis over the entire input image.

5. The apparatus of claim 3, wherein said array of photodetectors comprises an array of photomultiplier tubes (PMTs), and said pattern matching is performed on a PMT basis for all PMTs in said input image.

6. A method for spatial calibration of a gamma camera including a scintillation crystal and an array of photodetectors optically coupled to the scintillation crystal, comprising the steps of:
a) mounting a mask having a plurality of pinhole apertures arrayed in a non-rectangular distribution adjacent to said scintillation crystal;
b) scanning a point source of radiation over the entirety of said plurality of pinhole apertures;
c) collecting individual point source response data from each of said plurality of pinhole apertures;
d) modeling said point source response data as a Gaussian function;
e) generating at least one model patch from the collection of Gaussian model data;
f) pattern matching said simulated uniform flood image with an actual input image obtained using said mask to obtain a set of transformation factors; and
g) transforming said simulated uniform flood image using said transformation factors, to obtain a transformed uniform flood image that is used to correct input image data for spatial distortions.

7. The method of claim 6, wherein the step of pattern matching comprises the step of:
optimizing the minimization function $\Psi(X) = \int\int [f(x,y) - \Im_x\{g(x,y)\}]^2 dxdy$.

8. The method of claim 7, wherein the step of transforming comprises the step of applying a transformation function $$T_x\{g(x, y)\} = g\left(\frac{(x - x_0)}{l_x}, \frac{(y - y_0)}{l_y}\right)$$

where g(x,y) represents said Gaussian function data, $x_o$, $y_o$ represent displacement factors between g(x,y) and input image function data f(x,y), and $l_x$, $l_y$ represent magnification displacement factors between g(x,y) and f(x,y).

9. The method of claim 6, wherein the steps of pattern matching and transforming are applied to a global image patch.

10. The method of claim 6, wherein the steps of pattern matching and transforming are applied to PMT-based image patches.

11. The method of claim 6, wherein the steps of pattern matching and transforming are applied to a global image patch and to PMT-based image patches.

12. A method for spatial calibration of a gamma camera, comprising the steps of:
pattern matching an input image of a uniform flood radiation field imaged through a pinhole aperture mask, with a Gaussian model estimation of said uniform flood field, to obtain a set of transformation factors;
transforming said Gaussian model using said obtained set of transformation factors to obtain a transformed Gaussian model; and
using said transformed Gaussian model for spatial calibration of said gamma camera.

13. The method of claim 12, wherein the step of pattern matching comprises the step of: optimizing the minimization function $$\Psi(X) = \int\int [f(x, y) - \Im_x\{g(x, y)\}]^2 dxdy \qquad (6).$$

14. The method of claim 13, wherein the step of transforming comprises the step of applying a transformation function $$T_x\{g(x, y)\} = g\left(\frac{(x - x_0)}{l_x}, \frac{(y - y_0)}{l_y}\right)$$

where g(x,y) represents said Gaussian function data, $x_0$, $Y_0$ represent displacement factors between g(x,y) and input image function data f(x,y), and $l_x$, $l_y$ represent magnification displacement factors between g(x,y) and f(x,y).

* * * * *